United States Patent [19]

Eden

[11] 4,349,033
[45] Sep. 14, 1982

[54] INTRAUTERINE CATHETER

[76] Inventor: Robert D. Eden, 4265 Marina City Dr., Apt. 909WTN, Marina Del Ray, Calif. 90291

[21] Appl. No.: 204,591

[22] Filed: Nov. 6, 1980

[51] Int. Cl.³ .............................................. A61B 10/00
[52] U.S. Cl. ..................... 128/660; 128/774; 128/778; 128/349 B; 128/24 A
[58] Field of Search ........ 128/349 R, 349 B, 349 BV, 128/773, 778, 24 A, 660, 661–663, 774, 341, 348, 303.11

[56] References Cited

U.S. PATENT DOCUMENTS

| Re. 29,207 | 5/1977 | Bolduc et al. | 128/235 |
|---|---|---|---|
| 705,346 | 7/1902 | Hamilton . | |
| 3,312,215 | 4/1967 | Silber | 128/131 |
| 3,459,175 | 8/1969 | Miller | 128/654 |
| 3,779,234 | 12/1973 | Eggleton et al. . | |
| 3,817,248 | 6/1974 | Buckles et al. | 128/260 |
| 3,896,816 | 7/1975 | Mattler | 128/349 B |
| 3,938,502 | 2/1976 | Bom | 128/660 |
| 4,126,134 | 11/1978 | Bolduc et al. . | |
| 4,137,906 | 2/1979 | Akiyama et al. . | |

Primary Examiner—Kyle L. Howell
Assistant Examiner—Angela D. Sykes
Attorney, Agent, or Firm—Mitchell B. Wasson; Martin P. Hoffman

[57] ABSTRACT

An intrauterine catheter used in conjunction with an ultrasonic scanning apparatus to improve the resolution of the ultrasonic scan. The catheter consists of a catheter having an input orifice and a plurality of output orifices. A balloon substantially surrounds the entire catheter and is filled with a fluid through the catheter. A cervical sound stop is used to ensure that only the uterus is filled with the solution.

4 Claims, 2 Drawing Figures

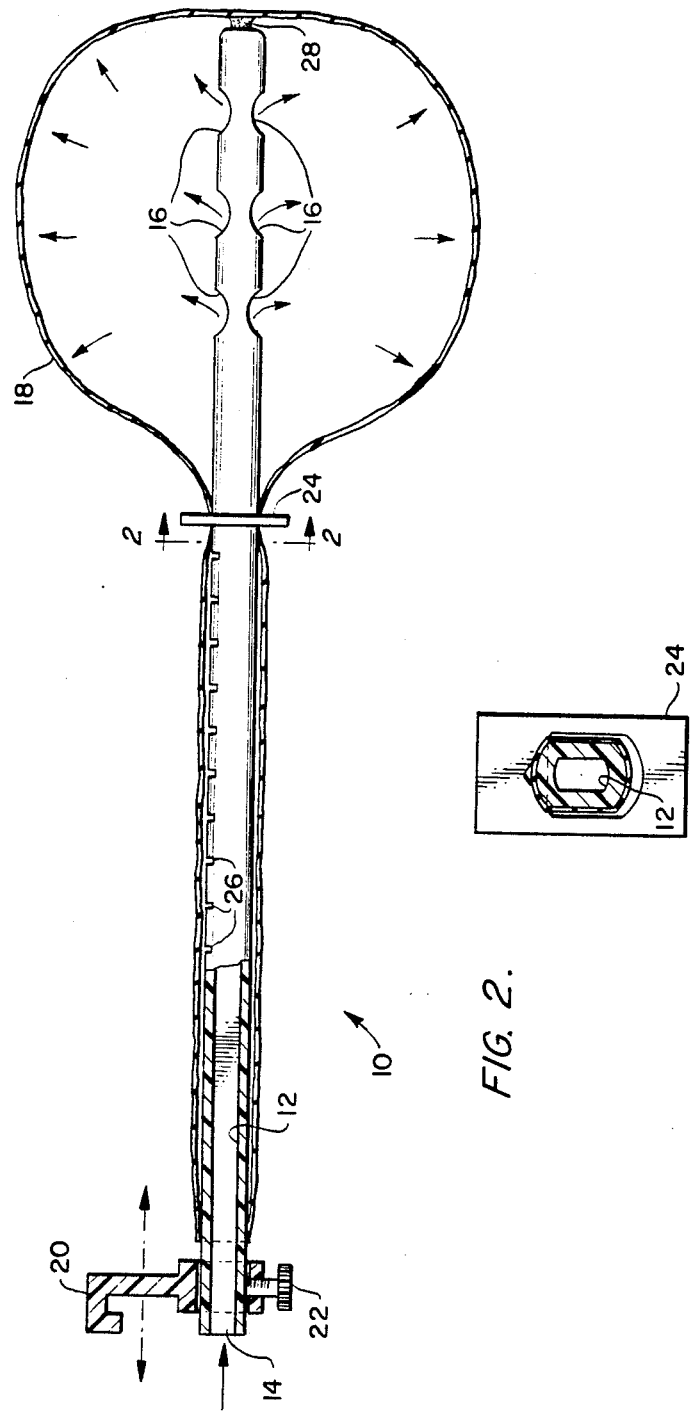

INTRAUTERINE CATHETER

BACKGROUND OF THE INVENTION

Ultrasonic scanning of the human body for diagnostic purposes has been widely used in the medical community. Typically, an ultrasonic transducer which generates ultrasonic waves is passed over a certain portion of the body. The waves are transmitted through the body and then reflected back to the transducer. These waves differ depending upon the density of a particular body tissue. The waves reflected back to the transducer are then transmitted to the device for reconstructing the ultrasonic waves which are presented for continuous viewing or for the production of a permanent record.

However, problems have arisen in certain ultrasonic scans due to poor resolution of the produced ultrasonic pictures. Some of these problems have been alleviated by placing the ultrasonic transducer in a fluid media which is then placed in contact with the patient's skins. These devices have proved effective in producing high resolution ultrasonic scans of body tissues in close proximity of the skin but are less effective for deeper tissues or body cavities.

U.S. Pat. No. 3,779,234 issued to Eggleton et al tried to provide good resolution for an ultrasonic scan of the heart by providing a transducer within a catheter provided in the heart. A balloon is provided around this catheter which is filled with a fluid to provide adequate resolution. It should be noted however, that the balloon does not enlarge sufficiently to cover the entire heart chamber and that the ultrasonic transducer must be placed within the organ to be studied. U.S. Pat. No. 3,938,502 issued to Bom also is directed to a catheter for providing an ultrasonic scan of an interior body organ, such as the heart, but makes no provision for producing a high resolution scan by injecting a fluid at, or near, to the ultrasonic transducer.

Therefore, although the prior art shows the use of improving ultrasonic scan resolution by injecting a fluid around a transducer, a device is needed to improve the resolution further by injecting fluid within a body cavity and utilizing an ultrasonic transducer placed over the portion of the scanned organ, but not directly within the organ.

SUMMARY OF THE INVENTION

The problems of the prior art are alleviated by the present invention by providing a fluid to the interior of a body cavity, such as a women's uterus while contemporaneously scanning the uterus with an ultrasonic transducer moving on top of the woman's skin over the uterus.

An elongated catheter containing a single opening at one end and a plurality of openings or holes at the other end is provided. A thin balloon is provided around the catheter in such a manner whereby a fluid introduced within the catheter by the first opening will enable the balloon to expand to the walls of the uterus. A cervical sound stop is provided to ensure that the fluid within the balloon is confined to the uterine cavity.

The catheter fills and distends the uterine cavity with fluid and allows the physician to ultrasonically visualize the endometrium, myometrium and serosal structures of the uterus. Additionally, visualization of pelvic structures, the fallopian tubes, ovaries and the cul-de-sac is improved. An ultrasonic scan or visualization is produced with the use of this catheter and allows excellent resolution and allows the doctor to accurately determine the presence of a pelvic mass, abnormal vaginal bleeding, pelvic cancer staging, congenital anomalies or pelvic infections. Additionally, such catheter will improve the ultrasonic scan which is required prior to surgical procedures such as laparoscopies, laparotomies, hysteroscopies, hysterosalpingograms, hysterectomies, hysterotomies or myomectomies.

Additionally, since the amount of fluid introduced into the balloon is carefully monitored, the volume and diameter of the uterus can be determined.

For a better understanding of the present invention, reference is made to the following description taken in connection with the accompanying drawings in which preferred embodiments of the invention are illustrated, the scope of the invention being pointed out and contained in the appended claims.

BRIEF DESCRIPTION OF THE DRAWINGS

FIG. 1 is a side elevational view of the catheter filled with fluid, and

FIG. 2 is a cross-sectional view taken through line 2—2 of FIG. 1.

BRIEF DESCRIPTION OF A PREFERRED EMBODIMENT

The catheter 10 of the present invention consists primarily of an elongated portion 12 and a thin plastic or rubber balloon 18 surrounding substantially the entire length of the catheter. The elongated portion is approximately 30 to 40 centimeters in length, is constructed of a very slightly malleable plastic and is formed with a hole 14 for the introduction of fluid to the interior of the catheter at one end and a plurality of holes 16 for allowing the fluid to exit from the catheter to the balloon 18 at its other end. Although FIG. 2 indicates that the elongated portion 12 is slightly oval in cross-section, this feature is not crucial, and the elongated portion could be round or elliptical in cross-section.

The balloon 18 has a capacity of approximately 200 cubic centimeters and surrounds substantially the entire length of the elongated portion 12. The balloon is permanently affixed to the portion 12 by glue or similar means at a point slightly forward of fill hole 14 and at a point 28 at the second end of the portion 12.

A hard plastic cervical sound stop 24 having an aperture therein is adapted to slide over the balloon 18 and elongated portion 12. A plurality of longitudinally spaced grooves 26 are placed approximately one centimeter apart on a portion of the elongated portion 12. The thickness of the grooves 26 and the cervical sound stop are equal therefore allowing the cervical sound stop 24 to pinch the balloon closed and prevent fluid contained in the balloon from flowing out of the balloon beyond the cervical sound stop 24. This stop 24 is important because it is placed at the woman's cervix allowing the balloon to expand only in the uterus. Since the balloon is thin enough to expand to the walls of the uterus and since the amount of fluid introduced into the catheter is measured, the size of the uterus can be determined. This knowledge is important in reaching certain diagnoses such as the presence of benign myoma tumors. It should be noted that this catheter could be utilized to positively determine the size of the uterus without proceeding with the ultrasonic scan.

The operation of the intrauterine catheter will now be described in detail: The patient is placed in the lithotomy position and a sterile speculum is used to visualize the cervix which is then grasped by a hard plastic single toothed tenaculum clamp 20. The uterus is then sounded with uterine sound to determine the length of the uterus. The cervical sound stop 24 is then placed into one of the grooves 26 on the elongated portion 12 at its desired length as determined by the uterine sound. The catheter 10 is then inserted into the uterine cavity until the cervical sound stop 24 reaches the external os. The tenaculum clamp 20 is slid into place behind the cervical sound stop 24 and is locked into position by screw 22. This clamp is attached to the tenaculum and serves to hold the cervical sound stop 24 in place as well as to help ensure that the fluid introduced into the balloon does not flow beyond the cervical sound stop 24. The speculum is removed and the uterus returns to its normal position.

With the patient in a supine position, a syringe is attached to fill hole 14 and a fluid such as water, a saline solution or dextran is introduced into the elongated portion 12 of the catheter. Altough the exact nature of the fluid is not crucial, it has been found that heavier fluids such as dextran, more effectively fill the balloon 18. Prior to the introduction of the fluid, the uterus is scanned with an ultrasonic transducer and the interior of the uterus is visualized in real time. A typical ultrasonic scanner would be ADR, Model 2130. The scanning continues as the balloon is slowly filled with fluid as shown by the arrows in FIG. 1. When the balloon expands to completely fill the entire uterine cavity, the injection of fluid is discontinued and the amount of fluid introduced within the catheter is recorded. After the scanning is completed, which includes determining the diameter of the uterus, the tenaculum clamp is loosened and removed as is the catheter.

In this manner, an ultrasonic scan of high resolution is provided to the physician as well as the size and diameter of the uterus, thereby allowing the physician to be able to formulate a proper diagnosis.

While there has been described what is at present considered to be a preferred embodiment of this invention, it will be obvious to those skilled in the art that various changes and modifications may be made therein without departing from the invention, and it is therefore intended to cover all such changes and modifications as they fall within the true spirit and scope of the invention.

What is claimed is:

1. An intrauterine catheter for utilization with an exterior ultrasonic transducer comprising:
   (a) an elongated portion having at least one fill hole at a first end and at least one exit orifice at the second end, said elongated portion including a plurality of longitudinally spaced grooves;
   (b) a balloon substantially surrounding the entire length of said elongated portion including said second end and sealingly attached to said elongated portion adjacent said first end;
   (c) a cervical sound stop slidably positioned over said balloon and said elongated portion.

2. An intrauterine catheter in accordance with claim 1 further including a tenaculum clamp slidable over said elongated portion to positively hold said cervical sound stop in place.

3. The method of determining the size of the uterus including the steps of:
   (a) providing a catheter having at least one fill hole and at least one exit orifice, said catheter substantially surrounded by a balloon;
   (b) determining the approximate length of the uterus by uterine sound;
   (c) sliding a cervical sound stop to the proper position on the catheter as determined by the uterine sound;
   (d) filling said catheter with a fluid such that said balloon expands to completely fill the uterus; and
   (e) noting the amount of fluid used to fill said balloon, said amount corresponding to the size of the uterus.

4. A method of ultrasonically scanning a woman's uterus comprising the steps of:
   (a) providing a catheter including an elongated portion having at least one fill hole at a first end and at least one exit orifice at the second and, said elongated portion including the second end thereof substantially surrounded by a balloon;
   (b) determining the approximate length of the uterus by uterine sound prior to placing the catheter in the uterus;
   (c) sliding a cervical sound stop to the proper position on the catheter as determined by the uterine sound prior to placing the catheter in the uterus;
   (d) placing said catheter in the uterus;
   (e) filling said catheter with a fluid such that said balloon expands to cover the entire area of the uterine wall;
   (f) passing an exterior ultrasonic transducer over the area of the uterus; and
   (g) viewing the produced ultrasonic scan.

* * * * *